(12) United States Patent
Mochizuki et al.

(10) Patent No.: US 10,736,980 B2
(45) Date of Patent: Aug. 11, 2020

(54) ULTRAVIOLET STERILIZATION DEVICE

(71) Applicant: Nikkiso Co., Ltd, Tokyo (JP)

(72) Inventors: Hiroaki Mochizuki, Hakusan (JP); Shinya Watanabe, Hakusan (JP)

(73) Assignee: NIKKISO CO., LTD., Tokyo (JP)

( * ) Notice: Subject to any disclaimer, the term of this patent is extended or adjusted under 35 U.S.C. 154(b) by 0 days.

(21) Appl. No.: 16/285,770

(22) Filed: Feb. 26, 2019

(65) Prior Publication Data

US 2019/0184045 A1     Jun. 20, 2019

Related U.S. Application Data

(63) Continuation of application No. PCT/JP2017/030380, filed on Aug. 24, 2017.

(30) Foreign Application Priority Data

Aug. 30, 2016   (JP) ................................. 2016-168506

(51) Int. Cl.
| | |
|---|---|
| *A61L 2/10* | (2006.01) |
| *C02F 1/32* | (2006.01) |
| *B01J 19/12* | (2006.01) |

(52) U.S. Cl.
CPC .............. *A61L 2/10* (2013.01); *B01J 19/123* (2013.01); *C02F 1/32* (2013.01); *C02F 1/325* (2013.01)

(58) Field of Classification Search
USPC .................................................. 250/455.11
See application file for complete search history.

(56) References Cited

U.S. PATENT DOCUMENTS

| | | | | |
|---|---|---|---|---|
| 5,260,036 A | * | 11/1993 | Weigold | ................. B01D 53/70 422/186 |
| 5,374,404 A | | 12/1994 | Weigold | |
| 5,397,552 A | | 3/1995 | Weigold | |
| 5,413,768 A | | 5/1995 | Stanley, Jr. | |
| 2009/0169442 A1 | | 7/2009 | Levy et al. | |
| 2010/0206787 A1 | | 8/2010 | Rozenberg et al. | |
| 2014/0328985 A1 | | 11/2014 | Snowball | |
| 2015/0008167 A1 | * | 1/2015 | Shturm | ................... C02F 1/001 210/85 |

(Continued)

FOREIGN PATENT DOCUMENTS

| | | |
|---|---|---|
| JP | H07-509381 A | 10/1995 |
| JP | 2000-350987 A | 12/2000 |

(Continued)

OTHER PUBLICATIONS

Office Action dated Jun. 2, 2020 in corresponding JP Application No. 2017-232421.

*Primary Examiner* — Kiet T Nguyen
(74) *Attorney, Agent, or Firm* — Muncy, Geissler, Olds & Lowe, P.C.

(57) ABSTRACT

An ultraviolet sterilization device includes a processing chamber that houses a subject of sterilization and a light source that irradiates an interior of the processing chamber with ultraviolet light. A wall of the processing chamber has a stack structure including a first layer made of a fluororesin material and a second layer made of an ultraviolet reflective material, the first layer being provided on the inner side of the processing chamber. The light source includes an aluminum gallium nitride (AlGaN) based ultraviolet light emitting device.

8 Claims, 4 Drawing Sheets

(56) References Cited

U.S. PATENT DOCUMENTS

| | | | |
|---|---|---|---|
| 2015/0060692 A1* | 3/2015 | Chen | C02F 1/325 |
| | | | 250/435 |
| 2016/0200594 A1 | 7/2016 | Chen | |
| 2016/0207795 A1 | 7/2016 | Hanada | |
| 2017/0281812 A1* | 10/2017 | Dobrinsky | A61L 2/088 |
| 2017/0320755 A1 | 11/2017 | Chen | |

FOREIGN PATENT DOCUMENTS

| | | |
|---|---|---|
| JP | 2003-181450 A | 7/2003 |
| JP | 2004-154722 A | 6/2004 |
| JP | 2011-016074 A | 1/2011 |
| JP | 2012-512723 A | 6/2012 |
| JP | 2014-061483 A | 4/2014 |
| JP | 2014-530027 A | 11/2014 |
| JP | 2015-058097 A | 3/2015 |
| JP | 2016-175025 A | 10/2016 |
| WO | WO2015/046014 A1 | 9/2014 |
| WO | WO2015/069680 A1 | 5/2015 |

* cited by examiner

ULTRAVIOLET STERILIZATION DEVICE

RELATED APPLICATION

Priority is claimed to Japanese Patent Application No. 2016-168506, filed on Aug. 30, 2016, the entire content of which is incorporated herein by reference.

BACKGROUND OF THE INVENTION

1. Field of the Invention

The present invention relates to ultraviolet sterilization devices and, more particularly, to a technology of sterilizing a subject of treatment by irradiating the subject of treatment with ultraviolet light.

2. Description of the Related Art

It is known that ultraviolet light has sterilization capability. Devices that radiate ultraviolet light are used for sterilization in medical and food processing fronts. Devices that sterilize a fluid such as water continuously by irradiating the fluid with ultraviolet light are also used. One example is a device in which an ultraviolet LED is provided on the inner wall at a pipe end of a flow passage formed by a straight metal pipe.

In order to irradiate the fluid flowing in a straight tube passage with ultraviolet light with a high efficiency, it is desired to configure the inner wall surface of the flow passage to have a high ultraviolet reflectivity. Further, it is desired to form the inner wall surface of the flow passage by using a material that is not easily corroded by the fluid flowing in the flow passage.

SUMMARY OF THE INVENTION

In this background, one illustrative purpose of the present invention is to provide an ultraviolet sterilization device in which the efficiency of irradiating the fluid flowing in the flow passage with ultraviolet light is increased.

An ultraviolet sterilization device according to an embodiment includes a processing chamber that houses a subject of sterilization and a light source that irradiates an interior of the processing chamber with ultraviolet light. A wall of the processing chamber has a stack structure including a first layer made of a fluororesin material and a second layer made of of an ultraviolet reflective material, the first layer being provided on the inner side of the processing chamber.

According to this embodiment, the resistance of the inner surface of the processing chamber to corrosion is increased by configuring the inner surface of the processing chamber, using the first layer made of a fluororesin material. By providing the second layer made of an ultraviolet reflective material outside the first layer, the ultraviolet light transmitted through the first layer can be reflected by the second layer and returned to the processing chamber. This can increase the ultraviolet light intensity in the processing chamber and improve the sterilization efficiency.

The ultraviolet sterilization device may further include a flow passage which is provided outside the processing chamber and in which a fluid flowing in the processing chamber flows. At least a part of the wall of the processing chamber may be a partition wall positioned between the processing chamber and the flow passage, the partition wall being comprised of a stack structure including the first layer, the second layer, and the third layer of a fluororesin material stacked in the stated order, the first layer being positioned toward the processing chamber and the third layer being positioned toward the flow passage.

An end of the second layer of the ultraviolet sterilization device may be covered by a fluororesin material.

The stack structure may further include an adhesive layer that fills a gap between the first layer and the second layer.

The first layer may be made of polytetrafluoroethylene (PTFE).

The first layer may have a thickness of 3 mm or larger.

The first layer may be formed to have a uniform thickness.

The second layer may be made of aluminum (Al).

A surface of the second layer facing the first layer may be a mirror surface.

DETAILED DESCRIPTION OF THE INVENTION

The invention will now be described by reference to the preferred embodiments. This does not intend to limit the scope of the present invention, but to exemplify the invention.

A description will be given of an embodiment of the present invention with reference to the drawings. Like numerals are used in the description to denote like elements and the description is omitted as appropriate.

First Embodiment

Figure 1:
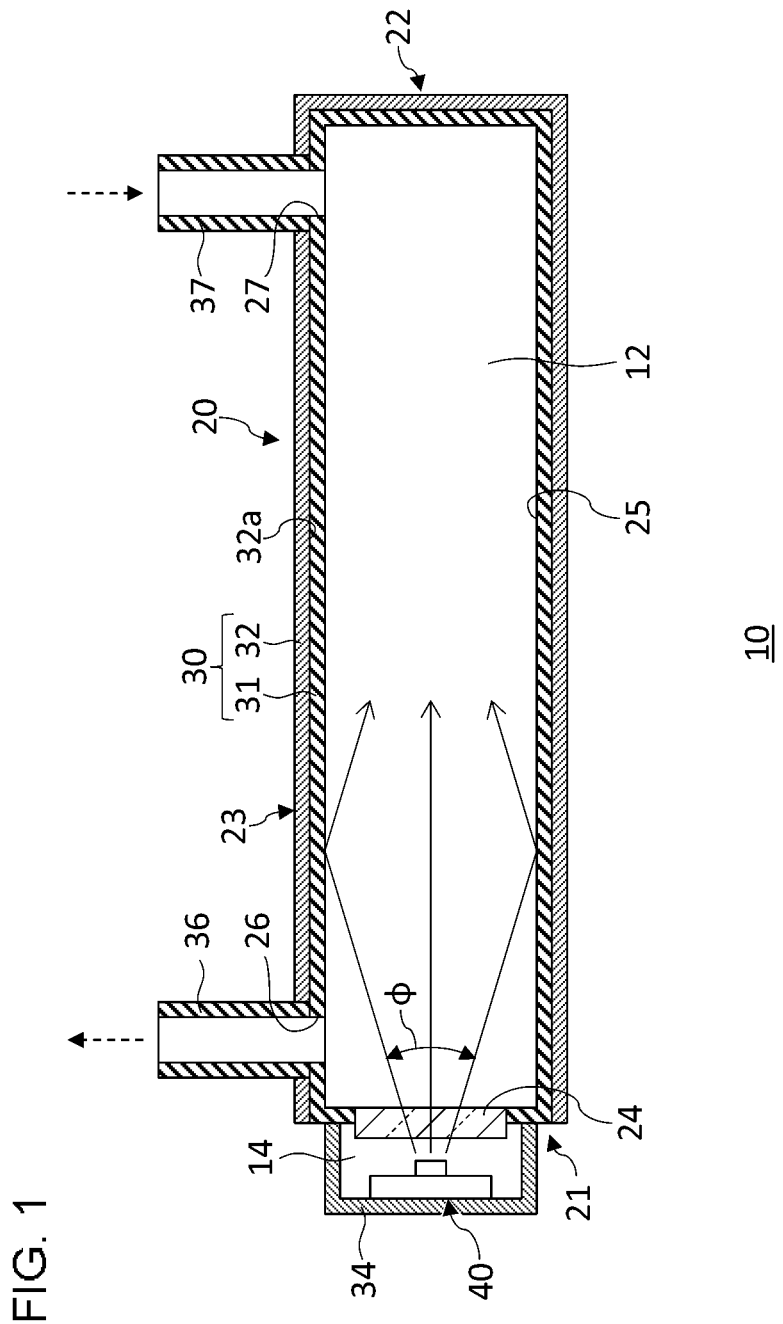
FIG. 1 is a cross-sectional view schematically showing a configuration of an ultraviolet sterilization device according to a first embodiment.

FIG. 1 is a cross-sectional view schematically showing a configuration of an ultraviolet sterilization device 10 according to a first embodiment. The ultraviolet sterilization device 10 includes a processing chamber housing 20, a light source chamber housing 34, an outflow tube 36, an inflow tube 37, and a light source 40. The light source 40 radiates ultraviolet light toward the interior of a processing chamber 12 encircled by the processing chamber housing 20. The ultraviolet sterilization device 10 is a fluid sterilization device to irradiate the fluid (water etc.) flowing in the processing chamber 12 with ultraviolet light so as to sterilize the fluid.

The processing chamber housing 20 is a container that defines the processing chamber 12. The processing chamber housing 20 has a first end wall 21, a second end wall 22, and a side wall 23. A window member 24 for transmitting the ultraviolet light from the light source 40 is provided on the first end wall 21. The second end wall 22 is provided at a position axially opposite to the first end wall 21. The side wall 23 extends from the first end wall 21 toward the second end wall 22 in the axial direction and has, for example, a shape of a cylinder or a square cylinder. The side wall 23 is provided with an outflow port 26 and an inflow port 27. The outflow port 26 is provided in the vicinity of the first end wall 21, and the inflow port 27 is provided in the vicinity of the second end wall 22. The outflow tube 36 is connected to the outflow port 26, and the inflow tube 37 is connected to the inflow port 27.

The wall of the processing chamber housing 20 is comprised of a stack structure 30 including a first layer 31 made of a fluororesin material and a second layer 32 made of an ultraviolet reflective material. The stack structure 30 is built such that the first layer 31 is provided on the inner side of the processing chamber 12 and the second layer 32 is provided on the outer side of the processing chamber 12. Thus, the first layer 31 is provided to cover an inner surface 32a of the second layer 32. An inner surface 25 of the processing chamber housing 20 is formed by the first layer 31, and the first layer 31 is exposed in the interior space of the processing chamber 12.

The fluororesin material forming the first layer 31 is exemplified by polytetrafluoroethylene (PTFE), perfluoroalkoxyalkane (PFA), perfluoro ethylene propylene copolymer (FEP), and amorphous fully fluorinated resin (e.g., CytopS (registered trademark) from AGC Inc., Teflon (registered trademark) AF from Dupont, etc.). In particular, PTFE is a chemically stable material having excellent durability, heat resistance, and chemical resistance and also has a high ultraviolet reflectivity. Therefore, PTFE is suitable as the material for the first layer 31.

For example, the first layer 31 is formed to have a uniform thickness over the entirety of the processing chamber housing 20. For example, the thickness of the first layer 31 is 3 mm or larger, and, preferably, 5 mm or larger. By configuring the first layer 31 to have a certain thickness or larger, the reflectivity of ultraviolet light incident on the inner surface 25 is increased. Our knowledge shows that, when the first layer 31 is made of PTFE, the diffuse reflectivity of ultraviolet light is ensured to be about 90% or higher by configuring the thickness of the first layer 31 to be 3 mm or larger.

The thickness of the first layer 31 may differ depending on the location. For example, the ultraviolet light intensity distribution in the interior space of the processing chamber 12 may be adjusted by varying the thickness of the first layer 31 in accordance with the distance from the light source 40. For example, the thickness of the first layer 31 may be configured to be smaller in the vicinity of the light source 40, and the thickness of the first layer 31 may be configured to be larger at a distance from the light source 40. Conversely, the thickness of the first layer 31 may be configured to be larger in the vicinity of the light source 40, and the thickness of the first layer 31 may be configured to be smaller at a distance from the light source 40. By configuring the thickness of the first layer 31 to be small, the contribution rate of the specular reflection component from the second layer 32 is increased. On the other hand, by increasing the thickness of the first layer 31, the contribution rate of the diffuse reflection component from the first layer 31 is increased.

The ultraviolet reflective material for forming the second layer 32 is exemplified by a metal material or a ceramic material. For example, aluminum (Al) having a high ultraviolet reflectivity can be used. Using a metal material such as aluminum for the second layer 32 can shield the ultraviolet light transmitted through the first layer 31 and prevent the ultraviolet light from leaking outside the processing chamber housing 20. It is preferred to mirror finish the inner surface 32a of the second layer 32 facing the first layer 31 to increase the ultraviolet reflectivity of the second layer 32.

The first layer 31 and the second layer 32 of the stack structure 30 may molded integrally or assembled together after the layers are molded separately. In the former case, the stack structure 30 may be formed by extrusion molding, injection molding, or the like. The second layer 32 may be formed by depositing aluminum on the outer side of the first layer 31. In the latter case, the first layer 31 may, for example, be fitted to the inner side of the second layer 32 formed in the shape of the processing chamber housing 20, or the second layer 32 may be fitted to the outer side of the first layer 31 formed in the shape of the processing chamber housing 20.

In the case that the first layer 31 and the second layer 32 are formed as separate parts, an adhesion layer filling the gap between the first layer 31 and the second layer 32 may be provided. By ensuring that an air layer is not created between the first layer 31 and the second layer 32, the ultraviolet reflectivity on the inner surface 32a of the second layer 32 is increased. It is preferred to use a fluororesin material having a high ultraviolet resistance in the adhesive layer between the first layer 31 and the second layer 32. Fluororesin such as an amorphous fluororesin having an adhesive group (CytopA (registered trademark) and CytopE (registered trademark) from AGC Inc., Algoflon from Solvay (registered trademark) AD, etc.) can be used for the adhesive.

The stack structure 30 may be used in the entire wall of the processing chamber housing 20 or only in a part of the wall of the processing chamber housing 20. It is preferred that the stack structure 30 be used at least in a portion directly irradiated with the ultraviolet light from the light source 40. Meanwhile, the stack structure 30 may not be used in a portion not likely to be directly irradiated with the ultraviolet light from the light source 40. For example, as illustrated, the second end wall 22 and the side wall 23 may be formed by a double-layer structure including the first layer 31 and the second layer 32, but the first end wall 21 may be formed by a single-layer structure including the first layer 31. In one variation, the first end wall 21 may be formed by the stack structure 30.

A further member may be used in the wall of the processing chamber housing 20 in addition to the stack structure 30. For example, a member made of a further material (e.g., a metal material or a resin material) may be fitted to the outer side of the stack structure 30. In other words, the stack structure 30 may be fitted as an inner wall of the processing chamber housing 20 relative to the further member forming the processing chamber housing 20.

The light source chamber housing 34 is provided adjacent to the first end wall 21 of the processing chamber housing 20 and defines a light source chamber housing the light source 40. The window member 24 is provided to partition between the processing chamber 12 and the light source chamber 14. The window member 24 is made of a material having a high ultraviolet transmittance such as quartz ($SiO_2$), sapphire ($Al_2O_3$), and amorphous fluororesin. The light source chamber housing 34 may be made of the same material as the processing chamber housing 20 or made of a different material. It is desired that the light source chamber housing 34 be made of a material capable of shielding ultraviolet light.

The outflow tube 36 and the inflow tube 37 are tubular members extending in the radial direction perpendicular to the axial direction of the processing chamber housing 20. It is preferred that the outflow tube 36 and the inflow tube 37 be made of a material having an excellent resistance to light and corrosion. It is desired that the tubes be made of a fluororesin material. The outflow tube 36 and the inflow tube 37 may be made of the same material as the first layer 31 and may be made of, for example, PTFE. The outflow tube 36 and the inflow tube 37 may be formed so as to be integrated with the first layer 31 forming a part of the side wall 23 or formed to be separate from the first layer 31 forming a part of the side wall 23 and joined to the first layer 31 later. Like the processing chamber housing 20, the outflow tube 36 and the inflow tube 37 may be comprised of a stack structure including the first layer 31 and the second layer 32.

In this embodiment, the outflow tube 36 is provided in the vicinity of the first end wall 21, and the inflow tube 37 is provided in the vicinity of the second end wall 22. In other words, the inflow tube 37 is provided at a position distanced from the light source 40, and the outflow tube 36 is provided at a position close to the light source 40. By configuring the device as described above, the fluid can be straightened from the inflow port 27 toward the outflow port 26, and the straightened fluid can be irradiated with high-intensity ultraviolet light in the vicinity of the light source 40.

The light source 40 is a so-called ultra violet-light emitting diode (UV-LED) that includes a light emitting device configured to emit ultraviolet light. It is preferred that the central wavelength or peak wavelength of the light emitting device included in the light source be included in a range of about 200 nm~350 nm and that the light emitting device emit ultraviolet light near 260 nm~270 nm having a high sterilizing efficiency. Such an ultraviolet LED is exemplified by an aluminum gallium nitride (AlGaN) based LED.

The light source 40 is provided in close proximity to the window member 24 and is arranged to irradiate the interior of the processing chamber 12 in the axial direction via the window member 24. The light source 40 may include an adjustment mechanism for adjusting the angle of light distribution of the light emitting device. In the case the directivity angle or orientation angle of the light emitting device included in the light source 40 is 60° or larger, 90° or larger, or 120° or larger, for example, the adjustment mechanism adjusts the output angle so that the angle of light distribution φ is 30° or smaller. The adjustment mechanism may be comprised of a transmission type optical system such as a lens or comprised of a reflection type optical system such as a concave mirror.

The adjustment mechanism ensures that the majority of the ultraviolet light output from the light source 40 enters the processing chamber 12 by adjusting the angle of light distribution φ. The adjustment mechanism may configure the angle of incidence of the ultraviolet light on the inner surface 25 of the processing chamber 12 to be 75° or larger. In particular, our knowledge shows that, in the case the inner surface 25 is made of PTFE, the reflectivity on the surface will be extremely high if the angle of incidence on PTFE is 70° or larger. For this reason, it is ensured that the ultraviolet light is reflected on the inner surface 25 of the processing chamber 12 with a high reflectivity and the high-intensity ultraviolet light can propagate a long distance in the processing chamber 12, by adjusting the angle of ultraviolet light distribution by using the adjustment mechanism.

The ultraviolet sterilization device 10 configured as described above irradiates the fluid flowing in the processing chamber 12 with the ultraviolet light from the light source 40 to sterilize the fluid. The fluid subject to the treatment flows in via the inflow tube 37 and flows in the processing chamber 12 from the inflow port 27 toward the outflow port 26. The light source 40 irradiates the fluid flowing in the processing chamber 12 in the axial direction from from the first end wall 21 toward the second end wall 22. A portion of the ultraviolet light from the light source 40 is incident on the inner surface 25 of the processing chamber housing 20 and propagates in the axial direction as it is reflected by the first layer 31 or the inner surface 32a of the second layer 32. The fluid irradiated with the ultraviolet light in the processing chamber 12 flows out via the outflow port 26 and the outflow tube 36.

According to this embodiment, the inner wall of the processing chamber housing 20 is comprised of the stack structure 30 including the first layer 31 made of a fluororesin material and the second layer 32 made of an ultraviolet reflective material so that the ultraviolet light output from the light source 40 can be used efficiently. By providing the first layer 31 made of a fluororesin material, the durability and resistance to corrosion of the inner surface 2 of the processing chamber housing 20 is increased. Further, the ultraviolet light is diffusely reflected by the first layer 31 to ensure uniform ultraviolet light intensity distribution inside the processing chamber 12. Further, by providing the second layer 32 having ultraviolet reflectivity, the ultraviolet light transmitted through the first layer 31 is reflected by the inner surface 32a of the second layer 32 and returned to the processing chamber 12. Further, the ultraviolet light is prevented from leaking outside the processing chamber housing 20. Still further, the second layer 32 is covered by the first layer 31 so that corrosion of the second layer 32 due to the fluid flowing in the processing chamber 12 is prevented and the high ultraviolet reflectivity of the inner surface 32a of the second layer 32 is maintained. With these functions and advantages, the embodiment provides an improved ultraviolet sterilization device 10 as compared with the case of forming the inner wall of the processing chamber housing 20 by only one of the first layer 31 and the second layer 32.

Second Embodiment

Figure 2:
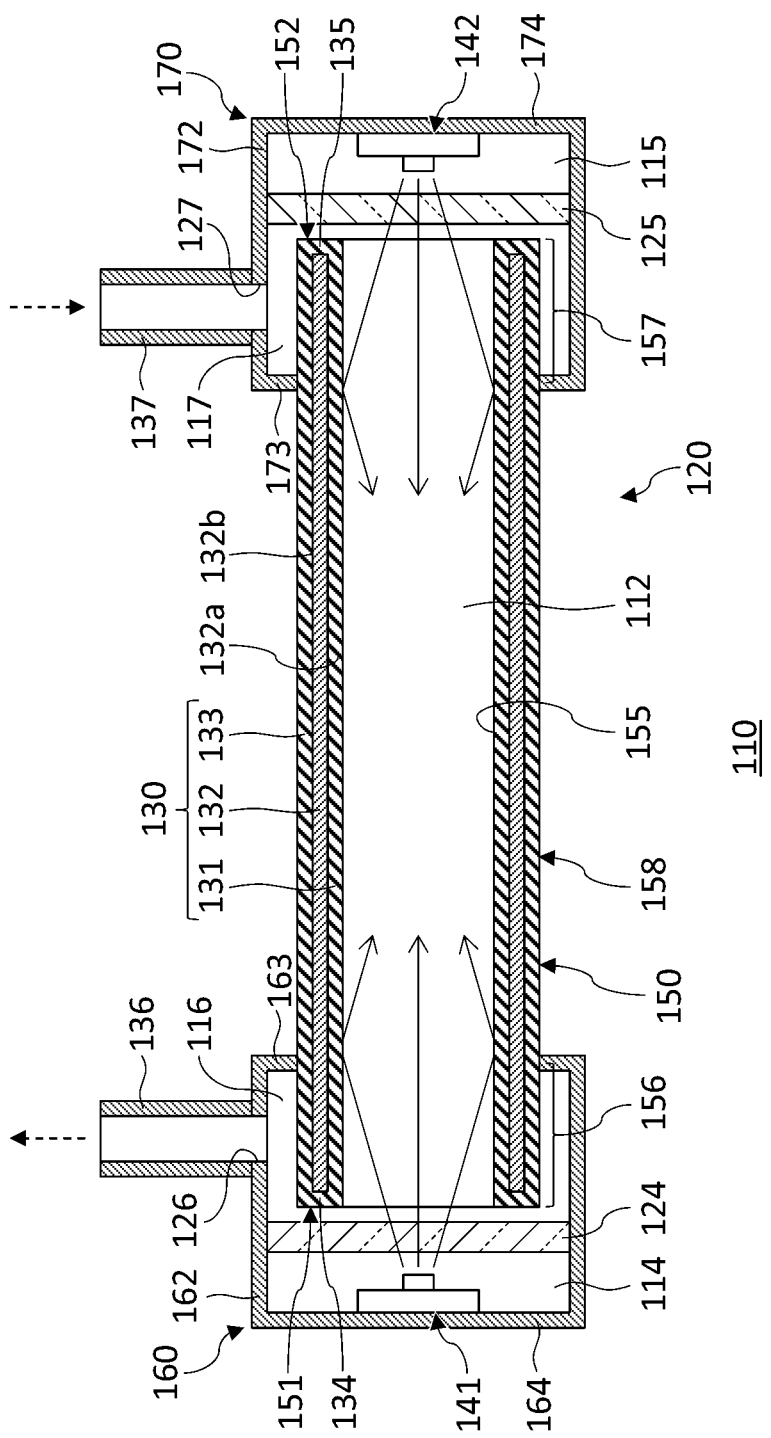
FIG. 2 is a cross-sectional view schematically showing a configuration of an ultraviolet sterilization device according to a second embodiment.

FIG. 2 is a cross-sectional view schematically showing a configuration of an ultraviolet sterilization device 110 according to a second embodiment. The ultraviolet sterilization device 110 includes a housing 120, a first light source 141, and a second light source 142. The housing 120 includes a processing chamber housing 150, a first light source chamber housing 160, and a second light source chamber housing 170. This embodiment differs from the embodiment described above in that the light sources 141, 142 are provided on both sides of a processing chamber 112, and straightening chambers 116, 117 are provided in the respective light source chamber housings 160, 170. The following description highlights the difference from the first embodiment.

The processing chamber housing 150 defines the processing chamber 112. The processing chamber housing 150 is a cylindrical member extending from a first end 151 toward a second end 152 in the axial direction and has, for example, a shape of a cylinder or a square cylinder. The first light source chamber housing 160 is provided at the first end 151, and the second light source chamber housing 170 is provided at the second end 152. The ends 151, 152 of the processing chamber housing 150 are open. The processing chamber 112 and the first straightening chamber 116 communicate at the first end 151, and the processing chamber 112 and the second straightening chamber 117 communicate at the second end 152.

The wall of the processing chamber housing 150 is comprised of a stack structure 130. The stack structure 130 includes a first layer 131 made of a fluororesin material, a second layer 132 made of an ultraviolet reflective material, and a third layer 133 made of a fluororesin material. The first layer 131, the second layer 132, and the third layer 133 of the stack structure 130 are stacked in the stated order. As illustrated, the stack structure 130 is arranged such that the first layer 131 is on the inner side of the processing chamber 112, and the third layer 133 is on the outer side of the processing chamber 112. Therefore, the first layer 131 is exposed in the interior space of the processing chamber 112 and forms an inner surface 155 of the processing chamber housing 150.

The second layer 132 includes an inner surface 132a facing the first layer 131 and an outer surface 132b facing the third layer 133. The inner surface 132a is a surface on which the ultraviolet light from the light sources 141, 142 is incident and is preferably mirror finished to increase the ultraviolet reflectivity. Meanwhile, the outer surface 132b is not a surface that reflects the ultraviolet light from the light sources 141, 142 and so need not be mirror finished. Both the inner surface 132a and the outer surface 132b may be mirror polished.

The stack structure further includes a first end protection part 134 and a second end protection part 135. The first end protection part 134 is provided to cover the end of the second layer 132 at the first end 151, and the second end protection part 135 is provided to cover the end of the second layer 132 at the second end 152. The first end protection part 134 and the second end protection part 135 covers the ends of the second layer 132 so as not to expose the second layer 132 at the ends 151, 152 of the processing chamber housing 150.

The first end protection part 134 and the second end protection part 135 are made of a fluororesin material and may, for example, be made of the same material as the first layer 131 or the third layer 133. In case the first layer 131 and the third layer 133 are made of PTFE, the first end protection part 134 and the second end protection part 135 may be made of PTFE. In one variation, the first layer 131, the third layer 133, the first end protection part 134, and the second end protection part 135 may be made of different materials.

In the stack structure 130, the first layer 131, the second layer 132, the third layer 133, the first end protection part 134, and the second end protection part 135 are molded integrally. For example, the stack structure 130 is formed by extrusion molding such that the second layer 132 is covered by fluororesin materials. In one variation, the first layer 131, the second layer 132, the third layer 133, the first end protection part 134, and the second end protection part 135 may be molded separately, and the stack structure 130 may be formed by assembling these together.

The processing chamber housing 150 includes a first section 156, a second section 157, and a third section 158. The first section 156 is a section positioned in a certain range from the first end 151 in the axial direction and provided in the first light source chamber housing 160. The second section 157 is a section positioned in a certain range from the second end 152 in the axial direction and provided in the second light source chamber housing 170. The third section 158 is a section positioned between the first section 156 and the second section 157 and is positioned between the first light source chamber housing 160 and the second light source chamber housing 170.

The first section 156 is a part of the wall of the processing chamber 112 and is a partition wall positioned between the processing chamber 112 and the first straightening chamber 116. Similarly, the second section 157 is a part of the wall of the processing chamber 112 and is a partition wall positioned between the processing chamber 112 and the second straightening chamber 117. Therefore, the first section 156 and the second section 157 are configured to partition between the processing chamber 112 and the flow passages (the first straightening chamber 116, the second straightening chamber 117) outside the processing chamber 112, and both the first layer 131 and the third layer 133 are in contact with the fluid. Meanwhile, no flow passages are provided outside the third section 158 so that only the first layer 131 is in contact with the fluid in the third section 158. In one variation, the third layer 133 may not be provided in the third section 158, and the outer surface 132b of the second layer 132 may be exposed outside in the third section 158.

The first light source chamber housing 160 is provided to encircle the first end 151. The first light source chamber housing 160 includes a first side wall 162, a first inner end wall 163, and a first outer end wall 164. The first side wall 162 is a cylindrical member extending from the first inner end wall 163 to the first outer end wall 164 in the axial direction and is provided, for example, to be coaxial with the central axis of the processing chamber housing 150. The first inner end wall 163 is a member extending radially outward from the processing chamber housing 150 toward the first side wall 162 and has an annular shape or a frame shape. The first outer end wall 164 is a member provided at a position distanced from the first end 151 in the axial direction so as to be opposite to the first end 151 and has a disc shape or a rectangular shape. Therefore, the first inner end wall 163 and the first outer end wall 164 are provided at positions axially opposite to each other, sandwiching the first end 151.

A first window member 124 for transmitting the ultraviolet light from the first light source 141 is provided inside the first light source chamber housing 160. The first window member 124 is provided in the vicinity of the first end 151 so as to provide a gap of a small dimension relative to the first end 151. It is preferred that the first window member 124 be provided such that the gap from the first end 151 is uniform over the entire circumference of the first end 151. It is also preferred that the surfaces of the first end 151 and the first window member 124 facing each other be substantially parallel. This straightens the flow of the fluid flowing from the processing chamber 112 toward the first straightening chamber 116 and moderates a disturbance in the flow produced in the vicinity of the first end 151 of the processing chamber 112.

The first window member 124 partitions the interior of the first light source chamber housing 160 into the first light source chamber 114 and the first straightening chamber 116. The first light source chamber 114 is an area defined by the first window member 124, the first side wall 162, and the first outer end wall 164. The first straightening chamber 116 is an area defined by the first window member 124, the first section 156 of the processing chamber housing 150, the first side wall 162, and the first inner end wall 163. The first straightening chamber 116 is formed in an annular shape or a rectangular frame shape and provided to encircle the processing chamber 112 from outside in the radial direction in the vicinity of the first end 151.

The first light source chamber housing 160 is provided with an outflow port 126 and an outflow tube 136. The outflow port 126 is a communication port through which the fluid irradiated with ultraviolet light in the processing chamber 112 flows out and is provided at a position communicating with the first straightening chamber 116. For example, the outflow port 126 is provided in the first side wall 162 as illustrated. The outflow tube 136 is a connecting pipe fitted to the outflow port 126 and is configured such that a pipe or a tube connector for connection to the ultraviolet sterilization device 110 can be mounted.

The second light source chamber housing 170 is configured in a manner similar to that of the first light source chamber housing 160. The second light source chamber housing 170 is provided to encircle the second end 152 and defines a second light source chamber 115 and the second straightening chamber 117. The second light source chamber housing 170 includes a second side wall 172, a second inner end wall 173, and a second outer end wall 174.

The second side wall 172 is a cylindrical member extending from the second inner end wall 173 to the second outer end wall 174 in the axial direction. The second inner end wall 173 is a member extending radially outward from the processing chamber housing 150 toward the second side wall 172 and has an annular shape or a frame shape. The second outer end wall 174 is a member provided at a position distanced from the second end 152 in the axial direction so as to be opposite to the second end 152 and has a disc shape or a rectangular shape. The second inner end wall 173 and the second outer end wall 174 are provided at positions axially opposite to each other, sandwiching the second end 152.

A second window member 125 for transmitting the ultraviolet light from the second light source 142 is provided inside the second light source chamber housing 170. The second window member 125 is provided in the vicinity of the second end 152 so as to provide a gap of a small dimension relative to the second end 152. It is preferred that the second window member 125 be provided such that the gap from the second end 152 is uniform over the entire circumference of the second end 152. It is also preferred that the surfaces of the second end 152 and the second window member 125 facing each other be substantially parallel. This straightens the flow of the fluid flowing from the second straightening chamber 117 toward the processing chamber 112 and moderates a disturbance in the flow produced in the vicinity of the second end 152 of the processing chamber 112.

The second window member 125 partitions the interior of the second light source chamber housing 170 into the second light source chamber 115 and the second straightening chamber 117. The second light source chamber 115 is an area defined by the second window member 125, the second side wall 172, and the second outer end wall 174. The second straightening chamber 117 is an area defined by the second window member 125, the second section 157 of the processing chamber housing 150, the second side wall 172, and the second inner end wall 173. The second straightening chamber 117 is formed in an annular shape or a rectangular frame shape and provided to encircle the processing chamber 112 from outside in the radial direction in the vicinity of the second end 152.

The second light source chamber housing 170 is provided with an inflow port 127 and an inflow tube 137. The inflow port 127 is a communication port through which the fluid irradiated with ultraviolet light in the processing chamber 112 flows in and is provided at a position communicating with the second straightening chamber 117. For example, the inflow port 127 is provided in the second side wall 172 as illustrated. The inflow tube 137 is a connecting pipe fitted to the inflow port 127 and is configured such that a pipe or a tube connector for connection to the ultraviolet sterilization device 110 can be mounted.

The first light source 141 is provided inside the first light source chamber 114 and is arranged to output ultraviolet light toward the opening of the first end 151. The second light source 142 is arranged inside the second light source chamber 115 and is arranged to output ultraviolet light toward the opening of the second end 152. It is preferred to provide the first light source 141 and the second light source 142 so that the majority of the output ultraviolet light enters the processing chamber 112.

With the above-described configuration, the ultraviolet sterilization device 110 irradiates the fluid flowing in the processing chamber 112 with the ultraviolet light from the first light source 141 and the second light source 142 so as to sterilize the fluid. The fluid subject to the treatment flows in a series of flow passages formed by the inflow tube 137, the second straightening chamber 117, the processing chamber 112, the first straightening chamber 116, the outflow port 126, and the outflow tube 136. The first straightening chamber 116 straightens the flow of the fluid by using a gap provided uniformly between the first window member 124 and the first end 151. Similarly, the second straightening chamber 117 straightens the flow of the fluid by using a gap provided uniformly between the second window member 125 and the second end 152. The first light source 141 and the second light source 142 irradiate the fluid straightened and flowing in the processing chamber 112 with ultraviolet light. The ultraviolet light from the first light source 141 and the second light source 142 propagates in the axial direction as it is reflected by the first layer 131 forming the inner wall of the processing chamber housing 150 and the inner surface of the second layer 132.

The inner wall of the processing chamber housing 150 according to this embodiment is also comprised of a stack of the first layer 131 made of a fluororesin material and the second layer 132 made of an ultraviolet reflective material. Therefore, the same advantage as that of the first embodiment described above is achieved. Further, since the outer surface 132b of the second layer 132 is covered by the third layer 133 and the ends of the second layer 132 are covered by the protection parts 134, 135, corrosion is prevented from occurring due to the contact of the fluid with the second layer 132.

According to this embodiment, the first straightening chamber 116 and the second straightening chamber 117 are provided on both sides of the processing chamber 112. Therefore, a disturbance in the flow produced in the the processing chamber 112 is inhibited more successfully than in the first embodiment described above. In particular, it is easy to maintain the straightened state even when the average flow rate of the fluid flowing in the processing chamber 112 is increased in order to increase the processing capability of the ultraviolet sterilization device 110. Thus, the embodiment allows the ultraviolet light to effectively affect the fluid flowing in a less disturbed state and increasing the sterilization effect accordingly.

Third Embodiment

Figure 3:
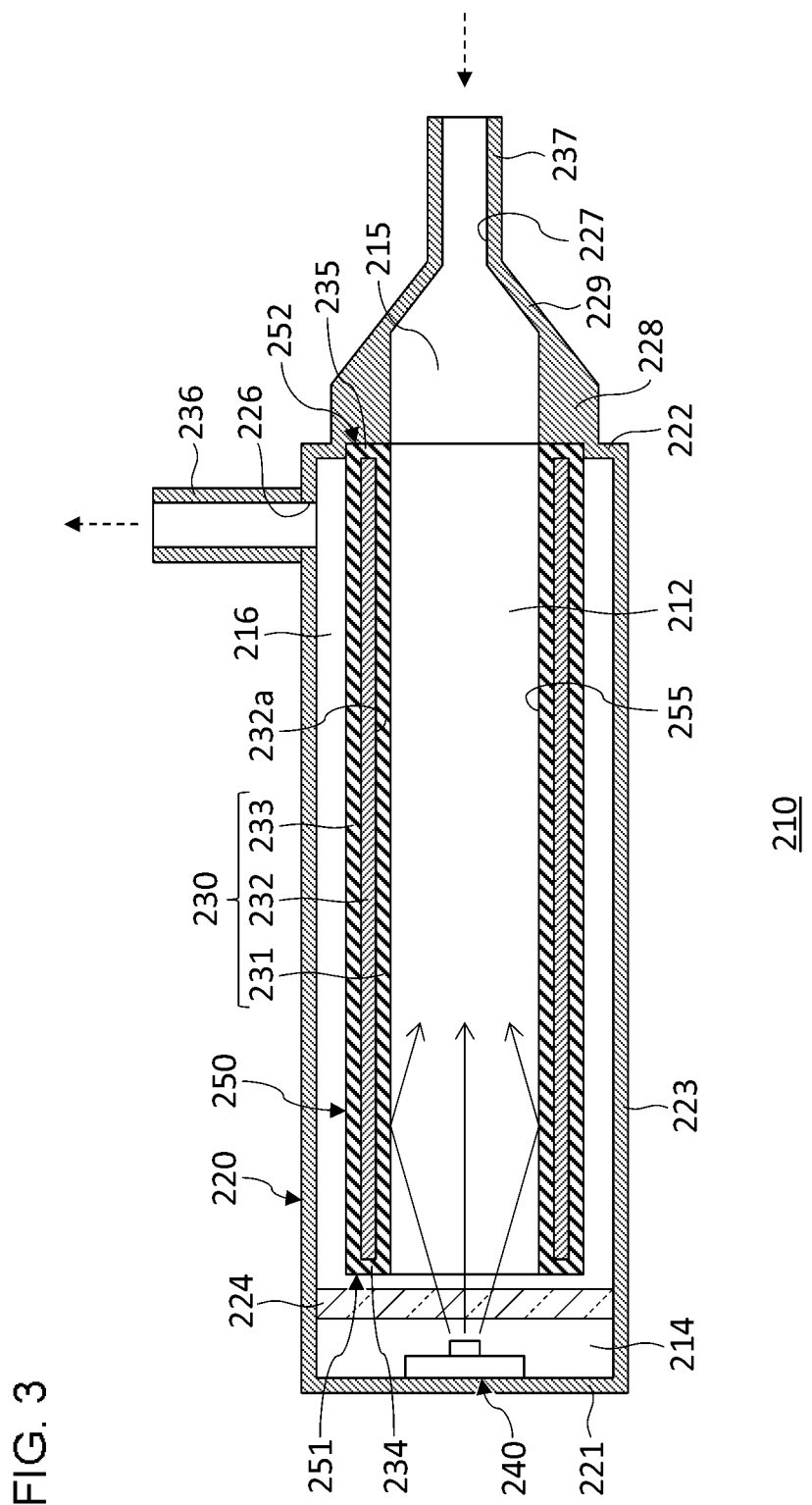
FIG. 3 is a cross-sectional view schematically showing a configuration of an ultraviolet sterilization device according to a third embodiment.

FIG. 3 is a cross-sectional view schematically showing a configuration of an ultraviolet sterilization device 210 according to a third embodiment. The ultraviolet sterilization device 210 includes a housing 220 and a light source 240. This embodiment differs from the embodiments described above in that a partition wall 250 is provided in the housing 220, and the interior of the housing 220 is configured as a dual structure including a processing chamber 212 and a straightening chamber 216. A description will now be given of the ultraviolet sterilization device 210, highlighting the difference from the embodiments described above.

The housing 220 includes a first end wall 221, a second end wall 222, a side wall 223, a window member 224, a connection end 228, a conical part 229, an outflow tube 236, an inflow tube 237, and the partition wall 250.

The partition wall 250 defines the processing chamber 112. The partition wall 250 is a cylindrical member extending from a first end 251 toward a second end 252 in the axial direction and has, for example, a shape of a cylinder or a square cylinder. The partition wall 250 is comprised of stack structure 230 including a first layer 231 made of a fluororesin material, a second layer 232 made of an ultraviolet reflective material, and a third layer 233 made of a fluororesin material. The stack structure 230 is arranged such that the first layer 231 is exposed in the processing chamber 212, and the third layer 133 is exposed in the straightening chamber 216. The inner surface 232a of the second layer 232 is preferably mirror polished. The stack structure 230 further includes a first end protection part 234, and a second end protection part 235 that cover the ends of the second layer 132.

The first end wall 221 is provided at a position distanced from the first end 251 in the axial direction so as to be opposite to the first end 251 in the axial direction. The second end wall 222 is provided in the vicinity of the second end 252 and extends radially outward from the partition wall 250. The side wall 223 is a cylindrical member extending from the first end wall 221 toward the second end wall 222 in the axial direction and has, for example, a shape of a cylinder or a square cylinder. The side wall 223 is provided with an outflow port 226, and an outflow tube 236 extending radially is fitted to the outflow port 226. The outflow port 226 is provided at a position distanced from the first end 251 in the axial direction and is provided at a position closer to the second end 252 than the first end 251.

The connection end 228 defines an inflow passage 215 communicating with the processing chamber 212. The second end 252 is connected to the connection end 228. The conical part 229 is a funnel-shaped member and connects the second end 252 with a relatively large diameter and an inflow port 227 with a relatively small diameter. The inflow tube 237 extending in the axial direction is connected to the inflow port 227.

The window member 224 is provided inside the housing 220 at a position facing the first end 251. The window member 224 partitions between the light source chamber 214 and the processing chamber 212 or the straightening chamber 216. The light source chamber 214 is defined by the first end wall 221, the side wall 223, and the window member 224. The light source 240 is provided inside the light source chamber 214. The straightening chamber 216 is defined by the second end wall 222, the side wall 223, the window member 224, and the partition wall 250. In this embodiment, the straightening chamber 216 extends along the processing chamber 212 in the axial direction and outside the processing chamber 212.

The ultraviolet sterilization device 210 configured as described above irradiates the fluid flowing in the processing chamber 112 with the ultraviolet light from the light source 240 to sterilize the fluid. The fluid subject to the treatment flows in a series of flow passages formed by the inflow tube 237, the inflow port 227, the inflow passage 215, the processing chamber 212, the straightening chamber 216, the outflow port 226, and the outflow tube 236. The ultraviolet light from the light source 240 propagates in the axial direction as it is reflected by the first layer 231 forming an inner surface 255 of the partition wall 250 and by the inner surface 232a of the second layer 232.

The same advantage as that of the foregoing embodiments described above is also achieved in this embodiment. According to this embodiment, the length of the straightening chamber 216 in the axial direction is longer than in the second embodiment so that the straightening effect of the straightening chamber 216 is increased. In particular, the first end 151 and the outflow port 226 are distanced in the axial direction so that the impact from any disturbance produced in the vicinity of the outflow port 226 is inhibited from reaching the first end 151. The inflow passage 215 is configured to be coaxial with the processing chamber 212 so that a disturbance is not easily produced in the flow of the fluid flowing into the processing chamber 212. Therefore, this embodiment makes the flow in the processing chamber 212 even more uniform and increases the efficiency of irradiating the fluid with ultraviolet light.

Fourth Embodiment

Figure 4:
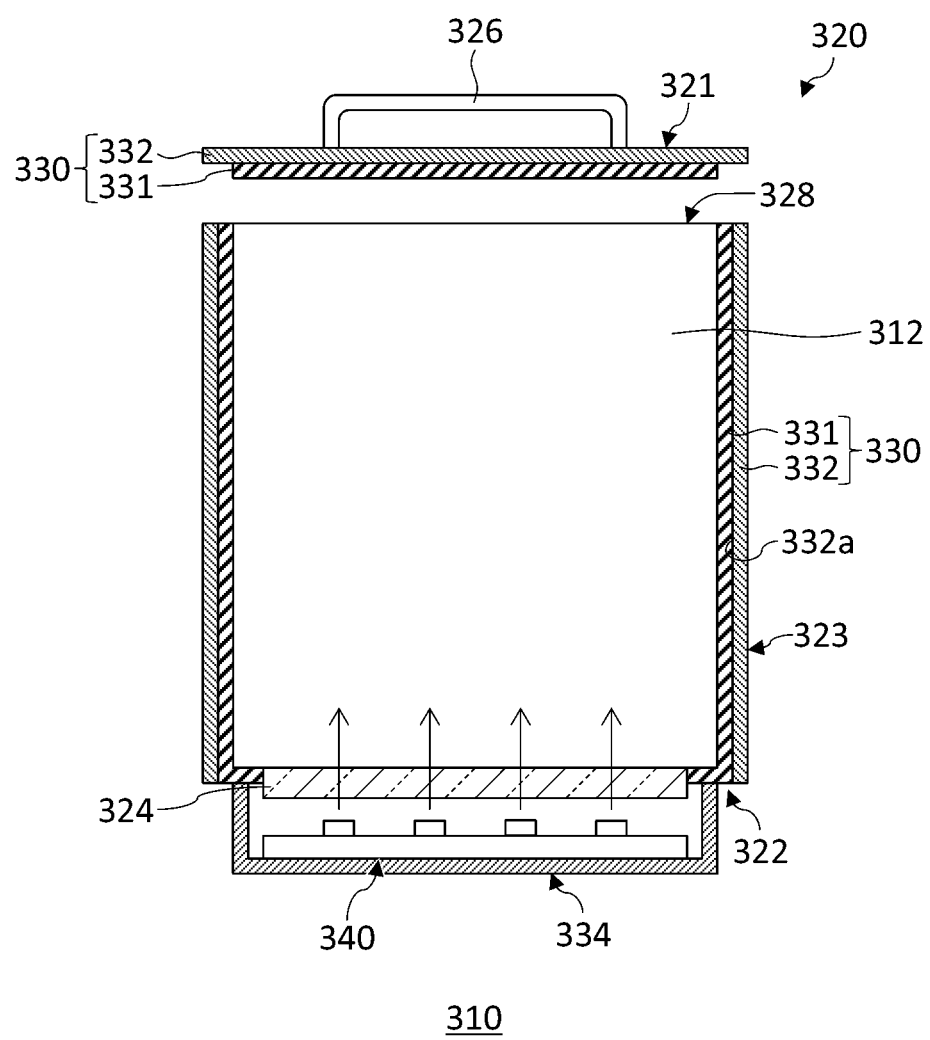
FIG. 4 is a cross-sectional view schematically showing a configuration of an ultraviolet sterilization device according to a fourth embodiment.

FIG. 4 is a cross-sectional view schematically showing a configuration of an ultraviolet sterilization device 310 according to a fourth embodiment. The ultraviolet sterilization device 310 includes a processing chamber housing 320, a light source chamber housing 334, and a light source 340, and the interior of a processing chamber 312 defined by the processing chamber housing 320 is irradiated with ultraviolet light. In this embodiment, the subject of the treatment is not sterilized continuously by the flow of the fluid. Instead, the subject of the treatment is housed or stored in the processing chamber 312 and sterilized by being irradiated with ultraviolet light. The following description of this embodiment highlights the difference from the embodiments described above.

The processing chamber housing 320 is a container encircling the processing chamber 312. The processing chamber housing 320 includes an upper lid 321, a bottom wall 322, and a side wall 323. The upper lid 321 is configured such that it is removable from the side wall 323 and is provided with a handle 326 for attachment and removal. The upper lid 321 is removed from the side wall 323 when the subject of the treatment is taken into or out of the processing chamber 312. The upper lid 321 is laid in an upper opening 328 of the side wall 323 when the interior of the processing chamber 312 is irradiated with ultraviolet light. The upper lid 321 may be configured such that it can be completely removed from the side wall 323. Alternatively, the upper lid 321 may be fitted to the side wall 323 via a hinge or the like.

The wall of the processing chamber 312 is comprised of a stack structure 330 including a first layer 331 made of a fluororesin material and a second layer 232 made of an ultraviolet reflective material. More specifically, the upper lid 321 and the side wall 323 are comprised of the stack structure 330. An inner surface 332a of the second layer 332 may be mirror polished. Meanwhile, the bottom wall 322 is provided with a window member 324 for transmitting ultraviolet light. The light source chamber housing 334 is fitted to the bottom wall 322, and the light source 340 is provided inside the light source chamber housing 334. The light source 340 is provided in an orientation in which it is capable of irradiating the interior of the processing chamber 312 with ultraviolet light via the window member 324.

Thus, according to this embodiment, the ultraviolet irradiation efficiency inside the processing chamber 312 is increased by configuring the wall of the processing chamber 312 of the storage type sterilization device to be comprised of the stack structure 330.

Described above is an explanation based on an exemplary embodiment. The embodiment is intended to be illustrative only and it will be understood by those skilled in the art that various design changes are possible and various modifications are possible and that such modifications are also within the scope of the present invention.

The device according to the embodiments and variations is described as a device for irradiating the fluid with ultraviolet light so as to sterilize the fluid. In a further variation, the inventive ultraviolet sterilization device may be used for a purification process that decomposes organic substance included in a fluid by using ultraviolet irradiation.

In a still further variation, the fluid may be caused to flow in a direction opposite to the direction of flow illustrated in the embodiments or variations described above. In other words, the inflow port and the outflow port may be used the other way around. In other words, the communication port denoted by the reference numeral 27 may be used as the outflow port and the communication port denoted by the reference numeral 26 may be used as the inflow port in the first embodiment shown in FIG. 1.

It should be understood that the invention is not limited to the above-described embodiment but may be modified into various forms on the basis of the spirit of the invention. Additionally, the modifications are included in the scope of the invention.

The invention claimed is:

1. An ultraviolet sterilization device comprising:
    a processing chamber which is configured as a cylinder that extends in an axial direction and in which a fluid that is a subject of sterilization flows;
    a light source provided to radiate ultraviolet light in the axial direction from an end of the processing chamber toward an interior of the processing chamber;
    a window member provided between the light source and the end of the processing chamber; and
    an outer flow passage which is provided outside the processing chamber and in which the fluid that is the subject of sterilization passing through the processing chamber flows,
    wherein a wall of the processing chamber is a stack structure including a first layer made of polytetrafluoroethylene (PTFE) having a thickness of 3 mm or larger and a second layer made of aluminum (Al), the first layer being provided on an inner side of the processing chamber, and
    at least a part of the wall of the processing chamber is a partition wall positioned between the processing chamber and the outer flow passage, the partition wall being a stack structure including the first layer, the second layer, and a third layer of a fluororesin material stacked in the stated order, and the first layer being positioned toward the processing chamber and the third layer being positioned toward the outer flow passage.

2. The ultraviolet sterilization device according to claim 1, wherein a surface of the second layer facing the first layer is a mirror surface.

3. The ultraviolet sterilization device according to claim 1, wherein
    an ultraviolet reflectivity of a surface of the second layer facing the third layer is lower than the surface facing the first layer.

4. The ultraviolet sterilization device according to claim 1, wherein
    the outer flow passage communicates with the interior of the processing chamber via a gap between the end of the processing chamber and the window member.

5. The ultraviolet sterilization device according to claim 1, wherein an end of the second layer facing the window member is covered by a fluororesin material.

6. The ultraviolet sterilization device according to claim 1, wherein the first layer is formed to have a uniform thickness.

7. An ultraviolet sterilization device comprising:
    a processing chamber which is configured as a cylinder that extends in an axial direction and in which a fluid that is a subject of sterilization flows;
    a light source provided to radiate ultraviolet light in the axial direction from an end of the processing chamber toward an interior of the processing chamber; and
    a window member provided between the light source and the end of the processing chamber,
    wherein a wall of the processing chamber is a stack structure including a first layer made of polytetrafluoroethylene (PTFE) having a thickness of 3 mm or larger and a second layer made of aluminum (Al), the first layer being provided on an inner side of the processing chamber, wherein
    the first layer is configured to have a thickness that varies in accordance with a distance from the light source.

8. The ultraviolet sterilization device according to claim 1, wherein the stack structure further includes an adhesive layer that fills a gap between the first layer and the second layer.

* * * * *